United States Patent [19]

Hwang

[11] Patent Number: 4,640,684

[45] Date of Patent: Feb. 3, 1987

[54] DENTAL DRILLING ASSEMBLY

[76] Inventor: Chong S. Hwang, 41-80 Parsons Blvd., Flushing, N.Y. 11355

[21] Appl. No.: 780,023

[22] Filed: Sep. 25, 1985

[51] Int. Cl.$^4$ .............................................. A61C 1/06
[52] U.S. Cl. .................................................... 433/110
[58] Field of Search ................................. 433/110, 111

[56] References Cited

U.S. PATENT DOCUMENTS

| 2,715,272 | 8/1955 | Pieper | 433/110 |
| 2,949,671 | 8/1960 | Flatland | 433/110 |
| 3,050,855 | 8/1962 | Ellis | 433/110 |
| 3,440,726 | 4/1969 | Ehrler et al. | 433/110 |

Primary Examiner—John J. Wilson
Attorney, Agent, or Firm—Birch, Stewart, Kolasch & Birch

[57] ABSTRACT

The present invention relates to a dental drilling assembly comprising an adjustable extension member which is utilized to vary the distance between pulley wheels of the drilling assembly to correspond to the size of the pulley utilized on the motor.

2 Claims, 3 Drawing Figures

4,640,684

DENTAL DRILLING ASSEMBLY

BACKGROUND OF THE INVENTION

The present invention relates to a dental drilling assembly and, more particularly, to a dental triple arm drilling apparatus which can be adapted for operation with both a small and a large size pulley disposed on the motor of the drilling assembly.

Motors which are utilized for operating drilling devices, for example, triple arm dental drilling assemblies, are provided with two size pulleys, that is, a small pulley and a large pulley which is attached directly to the motor. Thus, in the prior art, when it is desired to use the large pulley attached to the motor to achieve a slower rotational speed, it was necessary to use a triple arm drilling assembly which contained a large space between the wheels so that the drilling assembly was made compatible with the large pulley of the motor. On the other hand, when the small pulley of the motor was utilized in order to achieve a higher operational speed, it was necessary to replace the triple arm drilling assembly with a different drilling assembly which provided a narrow space between the side wheels thereof so that the assembly was compatible with the smaller pulley of the motor. The need to change the arms of the drilling assemblies to correspond to the size of the pulley utilized on the motor takes a long period of time and, thus, is very inconvenient.

OBJECTS AND SUMMARY OF THE INVENTION

Accordingly, it is an object of the present invention to provide an improved dental drilling assembly.

Another object of the present invention is to provide an improved dental drilling assembly which contains an adjustable extension element for changing the space between pulley wheels on the triple arm dental drilling assembly so as to make this assembly compatible with the particular pulley which is utilized on the motor.

A further object of the present invention is to provide an improved drilling assembly which is adjustable and, thus, is useable with different size pulleys which are attached to the motor.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The present invention is directed to a triple arm drilling assembly which can be modified by the use of an adjustable extension member which is placed between the large wheels of the drilling assembly in order to render the drilling assembly compatible with a particular pulley which is utilized on the motor. By the use of the adjustable extension member between the large wheels of the drilling device, the space between the large wheels can be adjusted to correspond to the large pulley on the motor. Such compatibility between respective pulleys on the drilling assembly and on the motor is established when the belt conveyed on the pulleys are in substantial parallel relationship with respect to each other. On the other hand, by removing the adjustable extension members, the distance between the large wheels of the drilling device is reduced to correspond with the small pulley utilized on the motor.

BRIEF DESCRIPTION OF THE DRAWINGS

The present invention will become more fully understood from the detailed description given hereinbelow and the accompanying drawings which are given by way of illustration only and, thus, are not limitative of the present invention, and wherein.

DETAILED DESCRIPTION OF THE INVENTION

Figure 1:
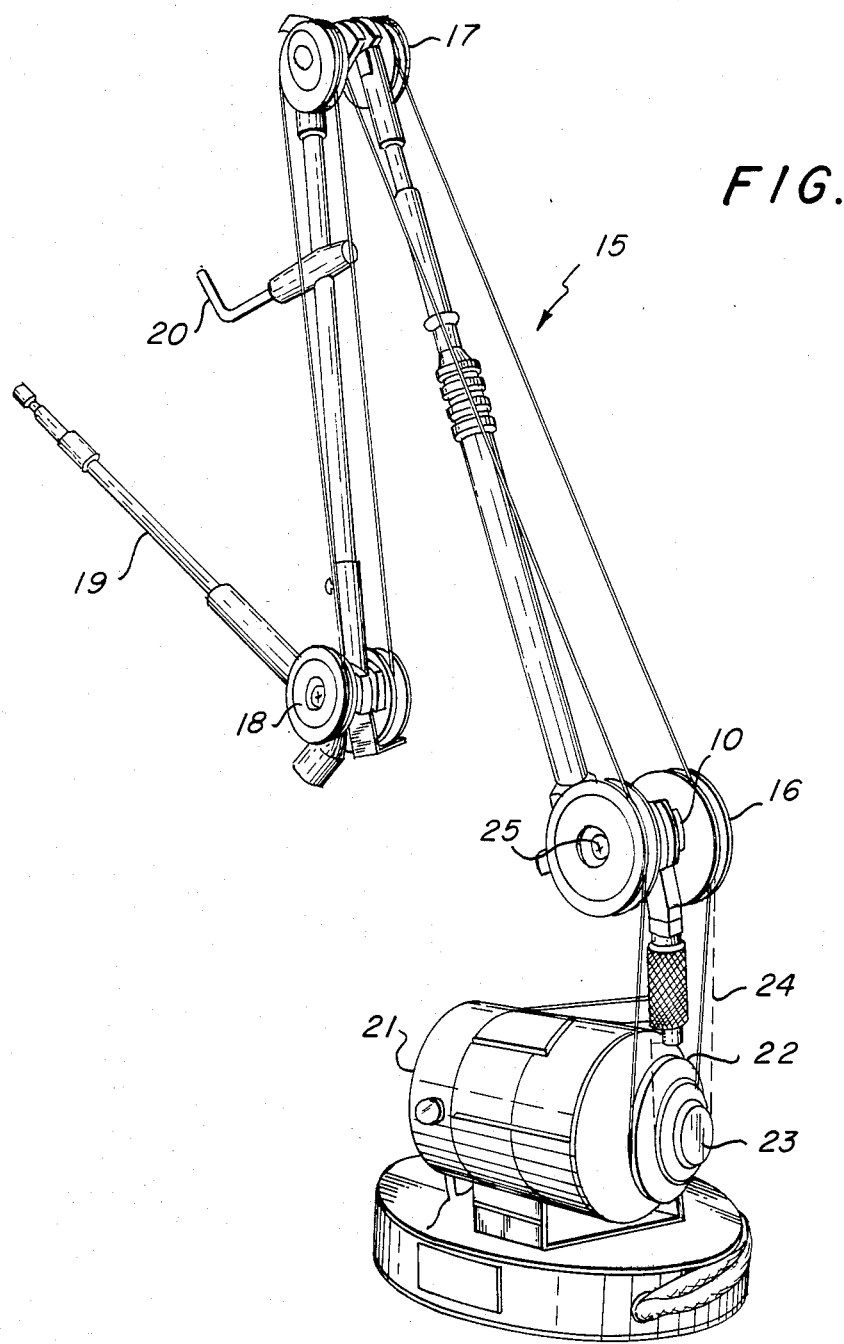
FIG. 1 is a perspective view of a triple arm dental drilling assembly of the present invention utilizing an adjustable extension member to make the drilling assembly correspond to the use of either a large or small size pulley disposed in the motor.
Figure 2:
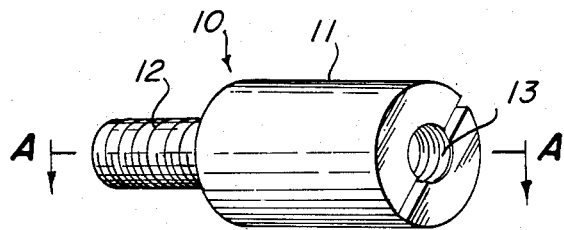
FIG. 2 is a perspective view of an adjustable extension member utilized in the present invention.
Figure 3:
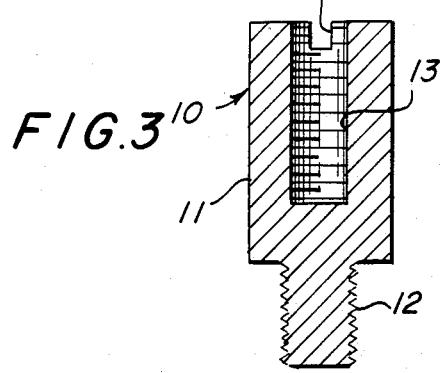
FIG. 3 is a cross-sectional view of the adjustable extension member of the present invention taken alone line A—A of FIG. 2.

Referring now in detail to the drawings for the purpose of illustrating the present invention, the improved dental drilling assembly as shown in FIG. 1 comprises an adjustable extension member 10 containing a body 11, a threaded end portion 12 disposed at end thereof, an inner threaded hole 13 disposed at the other end thereof and a slot 14 extending across the end of the extension member. The apparatus further includes a triple arm drilling assembly 15 having large wheels 16, small wheels 17 and 18, a hand piece 19 connected to the small wheels 18, a hanger 20, a motor 21 having both a large pulley 22 and a small pulley 23, and a belt 24 providing rotational communication between small wheels 17 and 18, large wheels 16 and either the large or small pulleys 22 and 23, respectively.

In operation, if it is desired to use the large pulley 22 on the motor 21, then the distance between the wheels 16 must be increased in order to make the pulleys 22 and 16 compatible and the belt 24 conveyed thereon in substantial parallel relationship. Thus, the space between the wheels 16 is enlarged by first removing the bolts 25 and the wheels 16 from the drilling assembly and using the threaded end portion 12 to screw the adjustable extension member into the location from which the bolt 25 was removed. The wheel 16 is then placed over the other end of the adjustable extension member and the bolt 25 is screwed into the threaded end portion 13 of the extension member. By the use of the adjustable extension member, the space between the pulley wheel 16 can be substantially increased. By utilizing the adjustable extension members at both sides of the pulley wheel 16, the distance between the pulley wheels can be further increased. The slot 14 is provided on the end of the adjustable extension member to provide a location for a screwdriver or other device for facilitating the attachment of the adjustable extension member. If it is desired to use the small pulley 23 on the motor, then the adjustable extension members can be removed and the pulley wheel 16 replaced in the manner discussed hereinabove. Thus, the device of the present invention makes it possible to utilize a single drilling assembly with a motor which is provided with multiple sized pulleys in order to achieve different operating conditions.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A triple arm dental drilling assembly containing arm members provided with pulley wheels and a motor provided with large and small size pulley wheels for conveying a belt member thereon, the improvement which comprises means for adjusting the distance between the arm pulley wheels that are closest to the motor, said means comprising a removably attached extension member inserted between said arm pulley wheels, whereby said extension member can be inserted between said arm pulley wheels to increase the distance therebetween to render them compatible with the large size pulley wheel on the motor, or can be removed to render them compatible with the small size pulley wheel on the motor.

2. The dental drilling assembly of claim 1, wherein the adjustable extension member has a body, a male threaded end portion at one end, a female threaded end portion at the other end and a slot provided at said female end portion.

* * * * *